(12) United States Patent
Lee et al.

(10) Patent No.: US 10,561,713 B2
(45) Date of Patent: Feb. 18, 2020

(54) HUNTER SYNDROME THERAPEUTIC AGENT AND TREATMENT METHOD

(71) Applicants: GREEN CROSS CORPORATION, Yongin-si, Gyeonggi-do (KR); MEDIGENEBIO CORPORATION, Yongin-si, Gyeonggi-do (KR)

(72) Inventors: Jin-Kyung Lee, Yongin-si (KR); Han-Yeul Byun, Yongin-si (KR); Myung-Eun Jung, Yongin-si (KR); Kyu-Hyun Lee, Yongin-si (KR)

(73) Assignees: GREEN CROSS CORPORATION, Yongin-si (KR); MEDIGENEBIO CORPORATION, Yongin-si (KR)

( * ) Notice: Subject to any disclaimer, the term of this patent is extended or adjusted under 35 U.S.C. 154(b) by 0 days.

(21) Appl. No.: 15/738,017

(22) PCT Filed: Jul. 4, 2016

(86) PCT No.: PCT/KR2016/007203
§ 371 (c)(1),
(2) Date: Dec. 19, 2017

(87) PCT Pub. No.: WO2017/003270
PCT Pub. Date: Jan. 5, 2017

(65) Prior Publication Data
US 2018/0303914 A1    Oct. 25, 2018

Related U.S. Application Data

(60) Provisional application No. 62/187,867, filed on Jul. 2, 2015.

(30) Foreign Application Priority Data

Dec. 28, 2015 (KR) ........................ 10-2015-0187297

(51) Int. Cl.
| | | |
|---|---|---|
| *A61K 38/46* | (2006.01) | |
| *A61K 9/00* | (2006.01) | |
| *A61K 38/16* | (2006.01) | |
| *A61P 3/00* | (2006.01) | |
| *A61K 47/02* | (2006.01) | |
| *A61K 47/18* | (2017.01) | |
| *A61K 47/26* | (2006.01) | |

(52) U.S. Cl.
CPC .......... *A61K 38/465* (2013.01); *A61K 9/0019* (2013.01); *A61K 38/16* (2013.01); *A61K 38/46* (2013.01); *A61K 47/02* (2013.01); *A61K 47/183* (2013.01); *A61K 47/26* (2013.01); *A61P 3/00* (2018.01); *C12Y 301/06013* (2013.01)

(58) Field of Classification Search
CPC ...... A61K 38/16; A61K 38/465; A61K 47/02; A61K 9/0019; A61K 47/26; A61K 38/46; A61K 47/183; A61P 3/00; C12Y 301/06013
See application file for complete search history.

(56) References Cited

U.S. PATENT DOCUMENTS

| | | |
|---|---|---|
| 8,545,837 B2 | 10/2013 | Zhu et al. |
| 2015/0086526 A1 | 3/2015 | Xie et al. |
| 2018/0228895 A1 | 8/2018 | Adler et al. |

FOREIGN PATENT DOCUMENTS

| | | | |
|---|---|---|---|
| JP | 2013224305 A | 10/2013 | |
| KR | 10-2010-0116558 A | 11/2010 | |
| KR | 10-1158673 B1 | 7/2012 | |
| KR | 10-1413947 B1 | 6/2014 | |
| WO | WO-2012177020 A2 * | 12/2012 | ........... A61K 38/465 |
| WO | 2013096912 A2 | 6/2013 | |

OTHER PUBLICATIONS da Silva et al. Enzyme replacement therapy with idursulfase for mucopolysaccharidosis type II (Hunter syndrome). Cochrane Database Syst Rev (2011), Issue 11, p. 1-25. (Year: 2011).*
European Patent Office, Communication dated Jan. 30, 2019, issued in corresponding European Application No. 16818303.6.
Felice et al., "Safety Evaluation of Chronic Intrathecal Administration of Idursulfase-IT in Cynomolgus Monkeys", Toxicologic Pathology, 2011, vol. 39, pp. 879-892 (14 pages total).
International Searching Authority, International Search Report of PCT/KR2016/007203 filed Oct. 10, 2016 [PCT/ISA/210].
Japanese Patent Office; Communication dated Oct. 30, 2018 in counterpart application No. 2017-568199.

* cited by examiner

*Primary Examiner* — Sean C. Barron
(74) *Attorney, Agent, or Firm* — Sughrue Mion, PLLC

(57) ABSTRACT

A Hunter syndrome therapeutic agent contains a first composition to be intravenously injected and a second composition to be subcutaneously injected. The agent can reduce the number of visits to the hospital by patients with Hunter syndrome to twice a month or less. It maintains a medicinal effect equivalent to or greater than that of a conventional once-a-week IV injection, increases drug-taking compliance of patients in comparison to conventional therapeutic agents and treatment methods, and enables enhanced patient welfare and convenience.

7 Claims, 14 Drawing Sheets

Specification includes a Sequence Listing.

[Fig. 1]
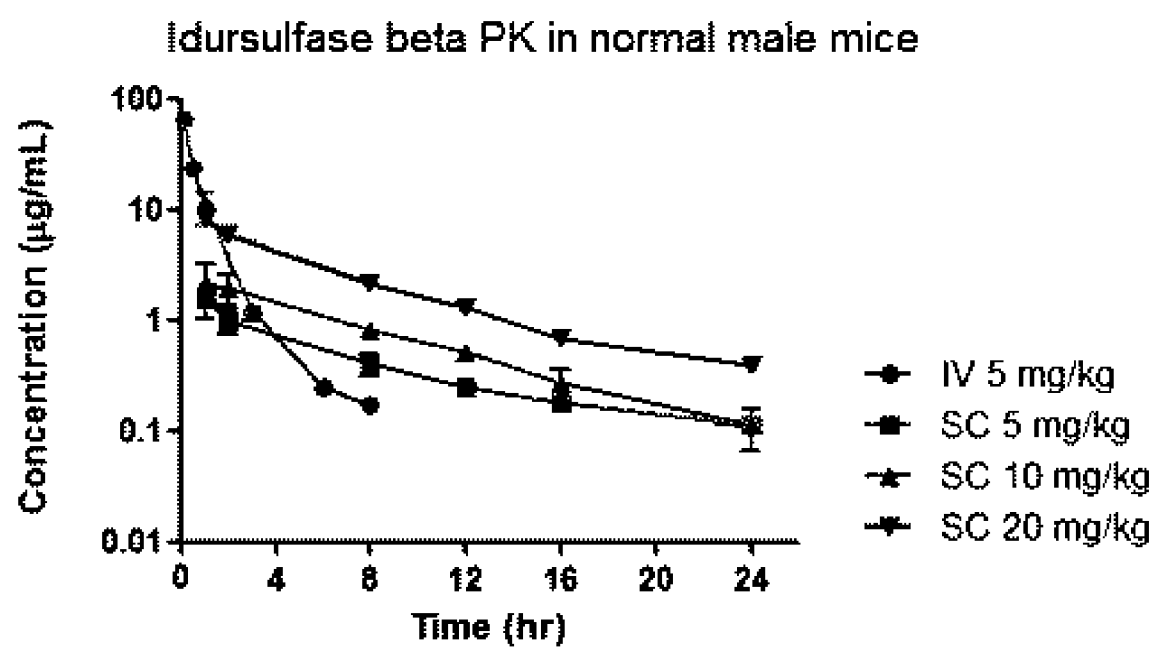

[Fig. 2(A)]
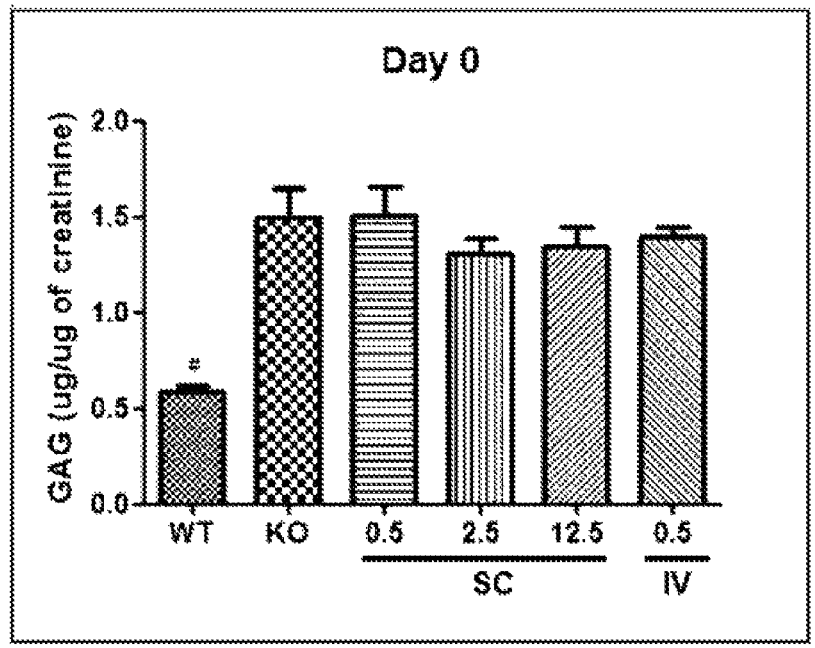
: p<0.05, ##: p<0.01, ###: p<0.001. vs KO.
Kruskal-Wallis Test and Dunn's Multiple Comparison Test
[Fig. 2(B)]
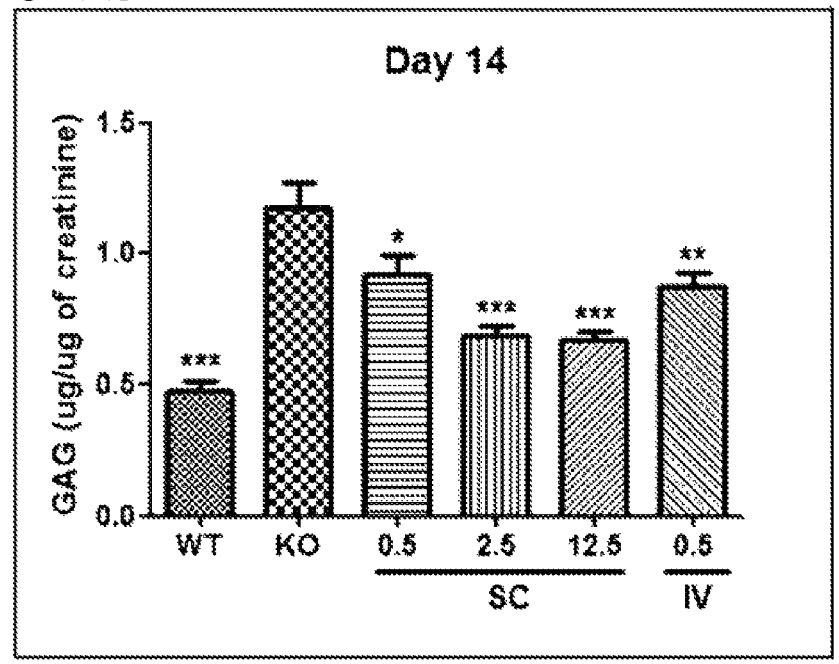
*: p<0.05, : p<0.01, *: p<0.001. vs KO.
One-way ANOVA and Dunnett's Multiple Comparison Test

[Fig. 2(C)]
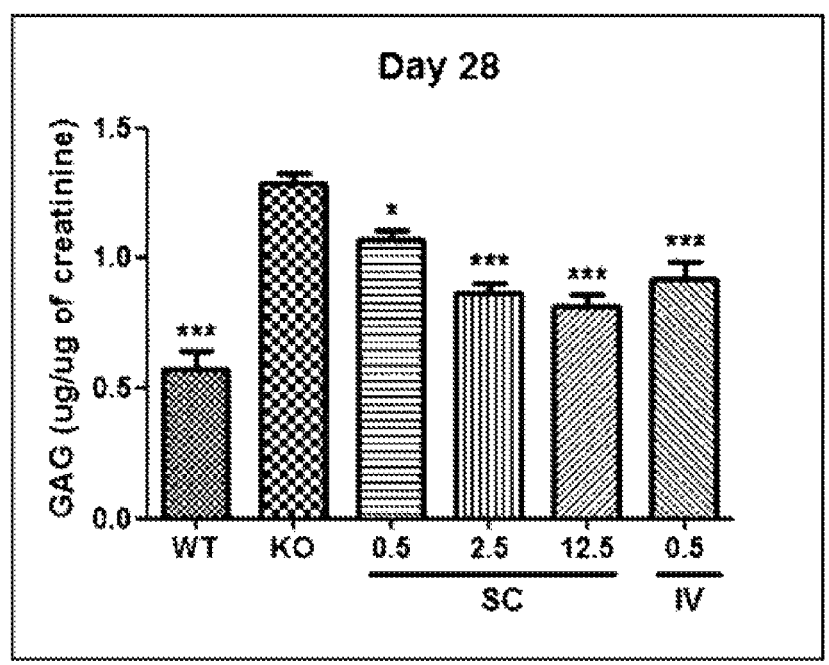

[Fig. 3]
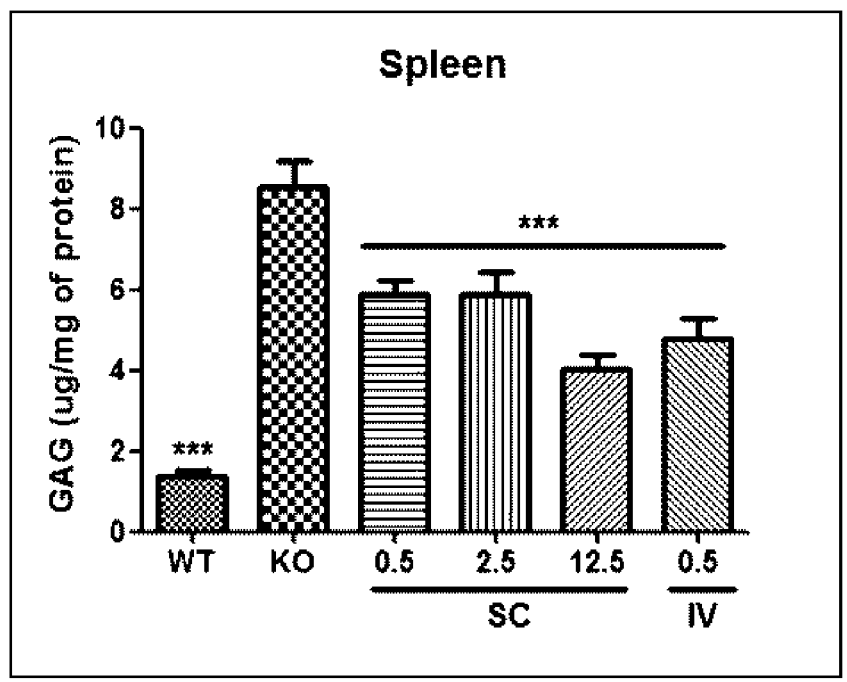
*: p<0.05, : p<0.01, *: p<0.001. vs KO.
One-way ANOVA and Dunnett's Multiple Comparison Test

[Fig. 4]
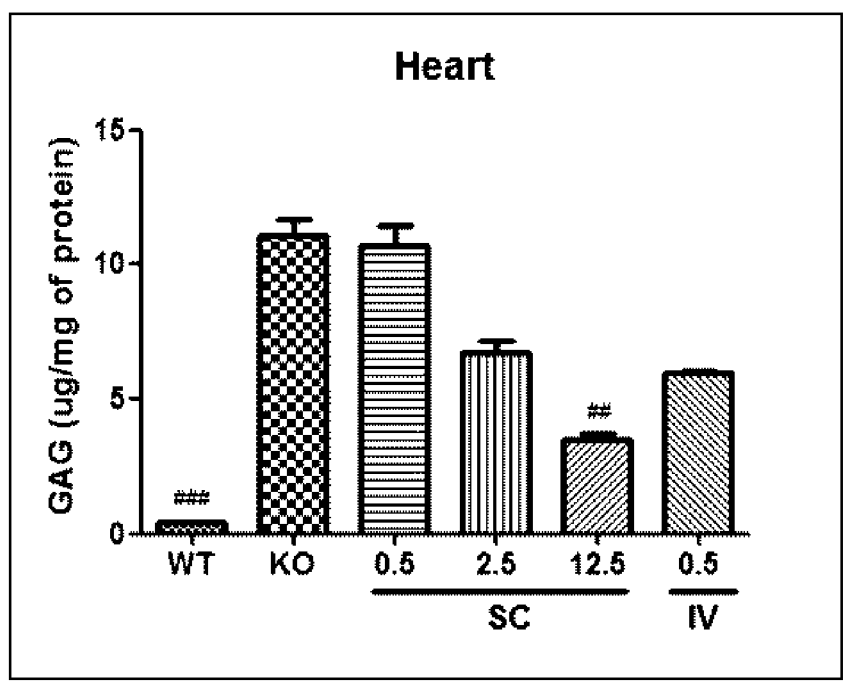
\#: p<0.05, \#\#: p<0.01, \#\#\#: p<0.001. vs KO.
Kruskal-Wallis Test and Dunn's Multiple Comparison Test

[Fig. 5]
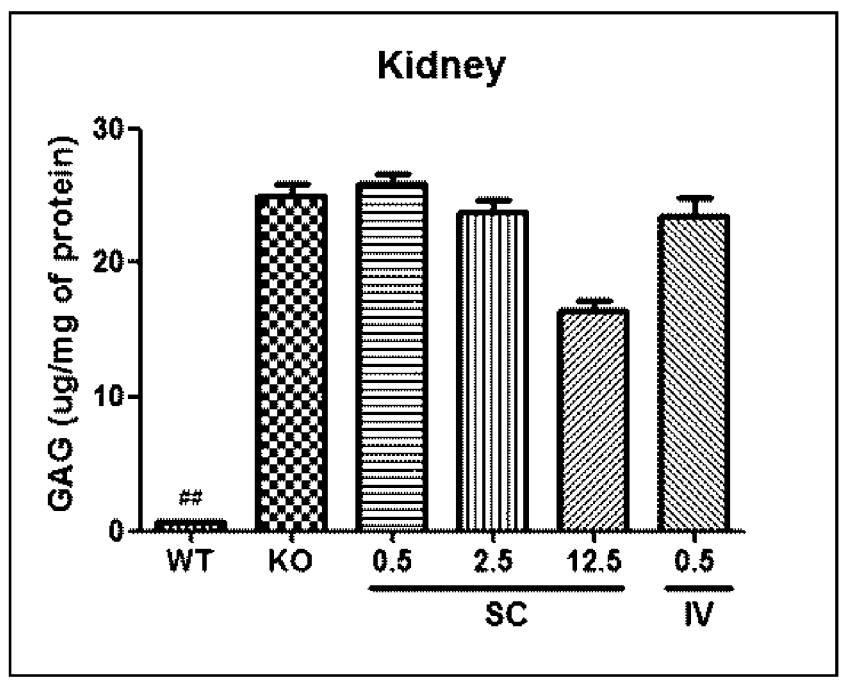
\#: p<0.05, \#\#: p<0.01, \#\#\#: p<0.001. vs KO.
Kruskal-Wallis Test and Dunn's Multiple Comparison Test

[Fig. 6]
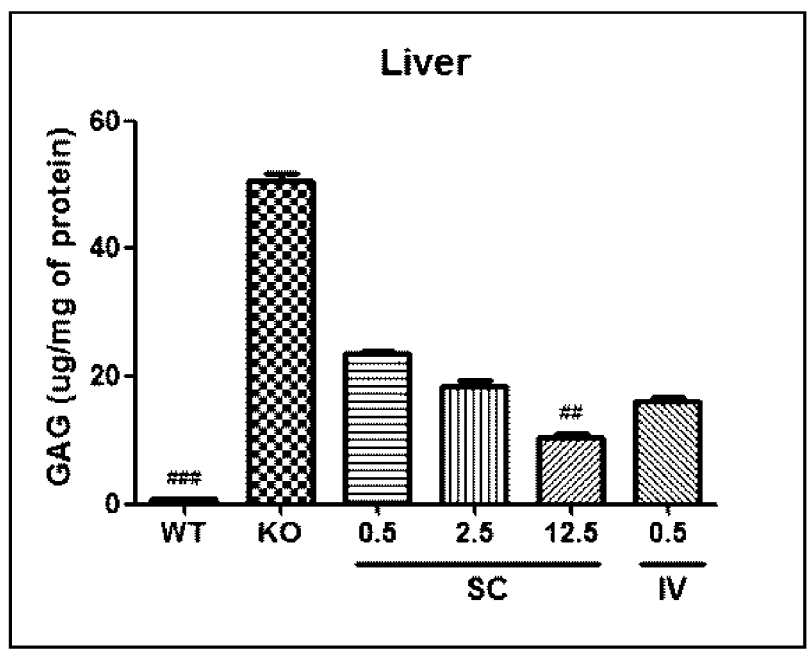
\#: p<0.05, \#\#: p<0.01, \#\#\#: p<0.001. vs KO.
Kruskal-Wallis Test and Dunn's Multiple Comparison Test
(GraphPad Prism)

[Fig. 7]
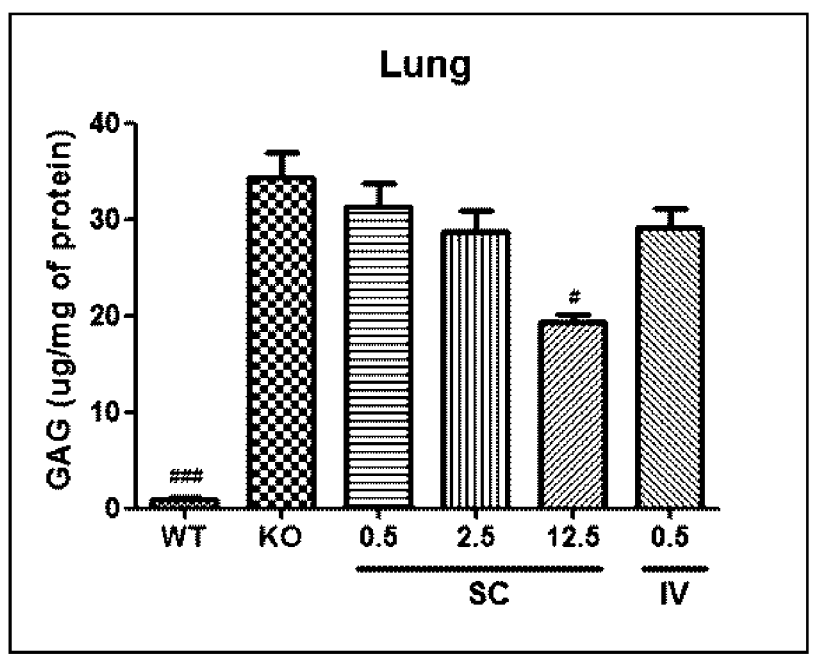
\#: p<0.05, \#\#: p<0.01, \#\#\#: p<0.001. vs KO.
Kruskal-Wallis Test and Dunn's Multiple Comparison Test
(GraphPad Prism)

[Fig. 8]
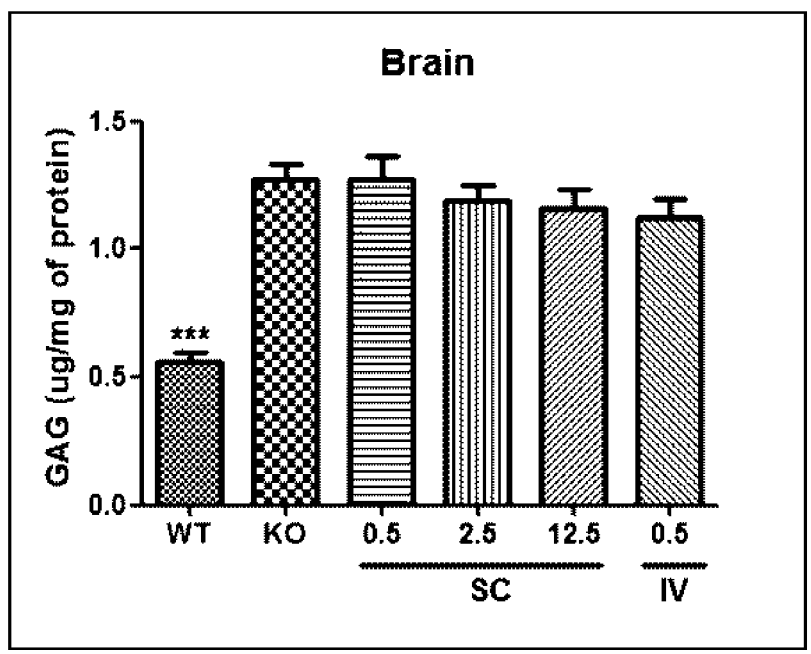
*: p<0.05, : p<0.01, *: p<0.001. vs KO.
One-way ANOVA and Dunnett's Multiple Comparison Test
(GraphPad Prism)

[Fig. 9]
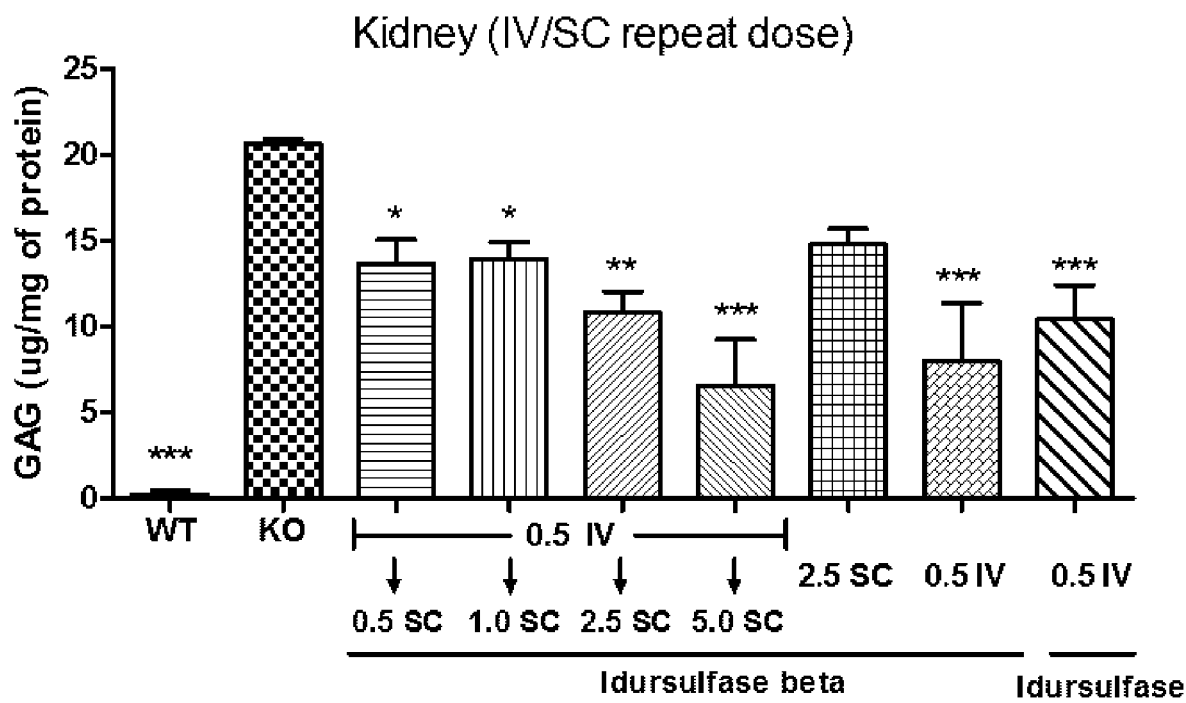

[Fig. 10]
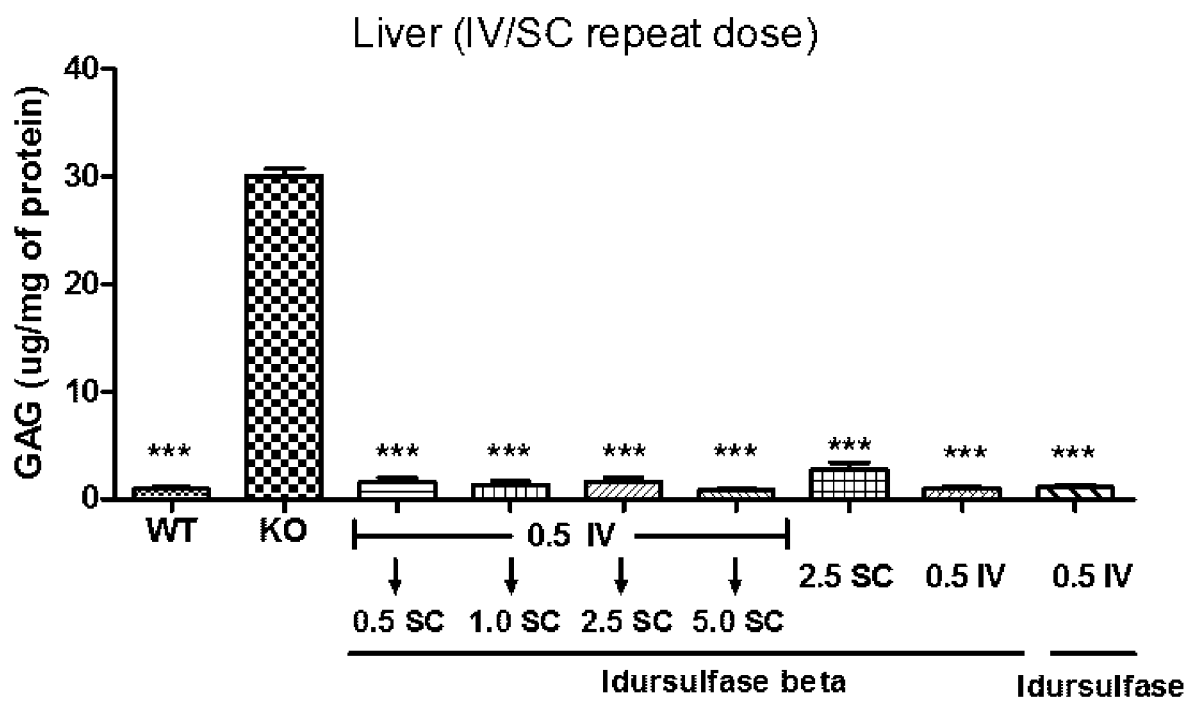

[Fig. 11]
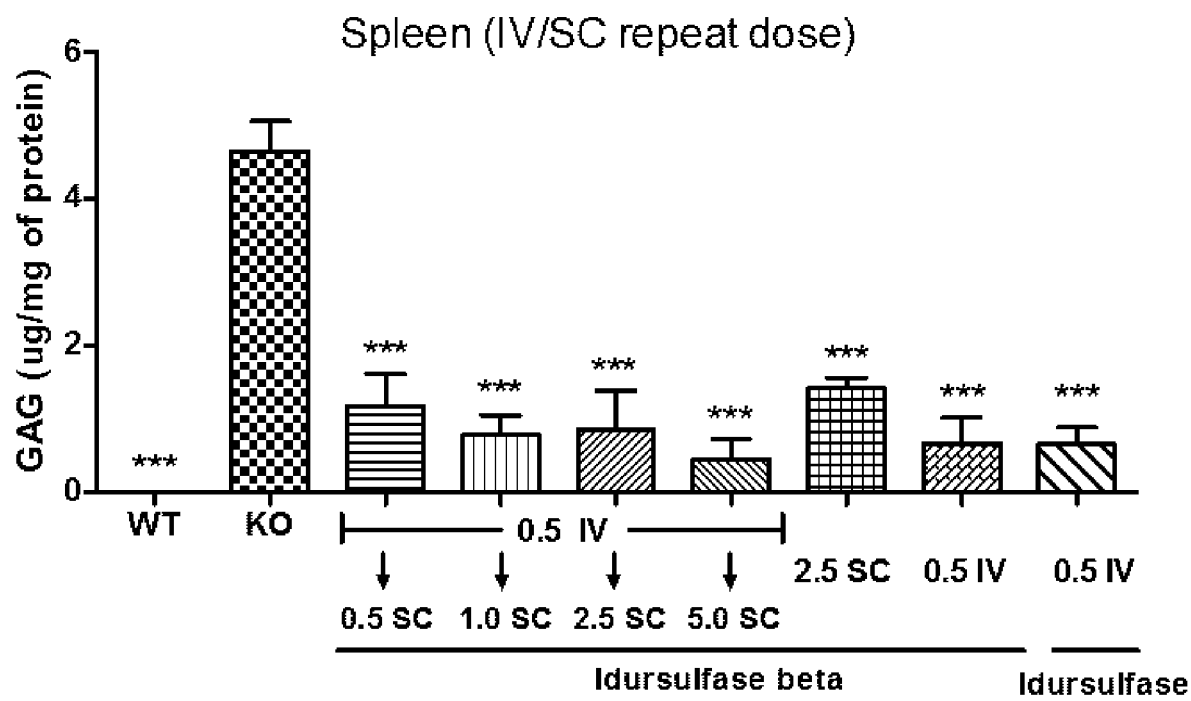

[Fig. 12(A)]
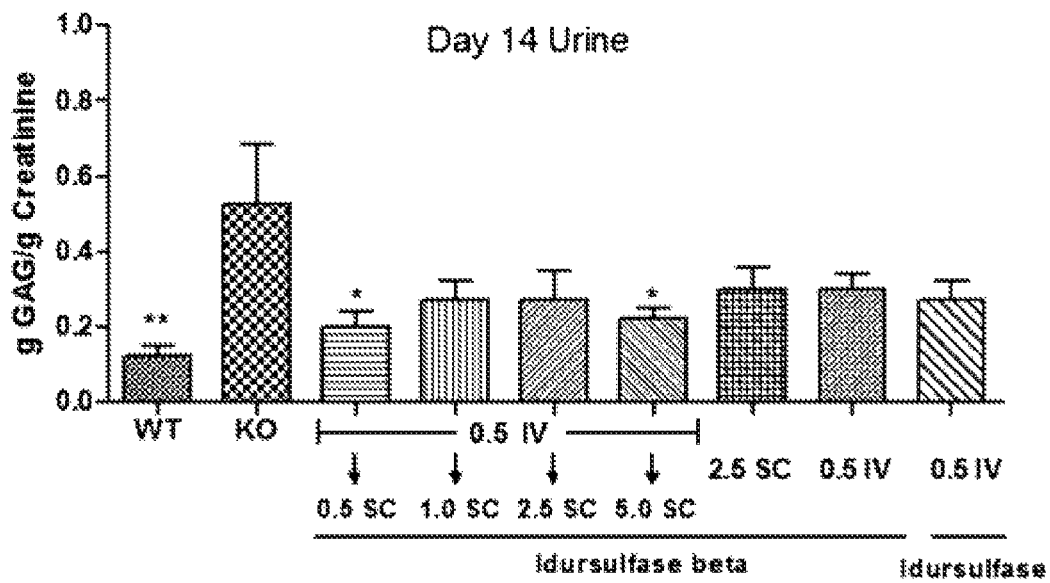
[Fig. 12(B)]
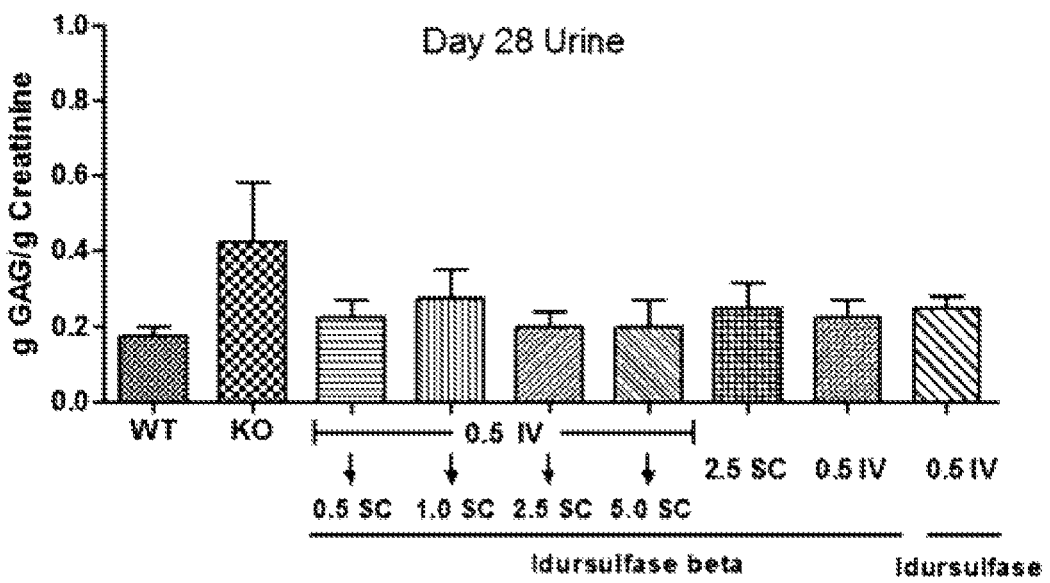

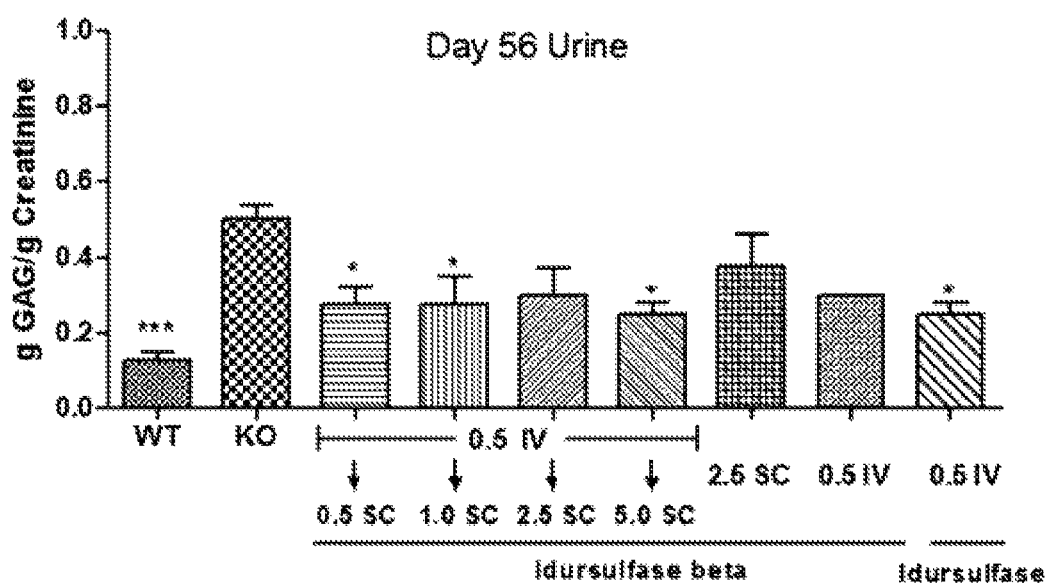
[Fig. 12(C)]

HUNTER SYNDROME THERAPEUTIC AGENT AND TREATMENT METHOD

CROSS REFERENCE TO RELATED APPLICATIONS

This application is a National Stage of International Application No. PCT/KR2016/007203, filed Jul. 4, 2016, claiming priority based on U.S. Provisional Application No. 62/187,867, filed Jul. 2, 2015 and Korean Application No. 10-2015-0187297, filed Dec. 28, 2015, the contents of all of which are incorporated herein by reference in their entirety.

TECHNICAL FIELD

The present invention relates to a formulation for treating Hunter syndrome and a method for treating Hunter syndrome with the same.

BACKGROUND ART

Hunter syndrome or mucopolysaccharidosis type II is one of the lysosomal storage diseases (LSD) in which mucopolysaccharides such as glycosaminoglycan (GAG) do not decompose to thereby accumulate in lysosomes due to a deficiency of iduronate-2-sulfatase (IDS). GAG accumulates in all cells of the body and causes various symptoms, which include prominent facial features, large head, and abdominal distension due to hypertrophy of the liver or spleen, and are accompanied by hearing loss, heart valve diseases, obstructive respiratory diseases, and sleep apnea. It may also involve a limitation of joint motion as well as nervous system symptoms and developmental delay caused by invasion of the central nervous system. Hunter syndrome is known to occur in about 1 out of 162,000 people and is inherited as an X-linked recessive form, which causes great pains for not only the patients but also their family members.

Up to the present, various methods have been attempted to treat Hunter syndrome, such as bone marrow transplantation, enzyme supplementation, gene therapy, and the like. The bone marrow transplantation has the disadvantages that although the symptom is significantly improved, it is difficult to find a donor whose human leukocyte antigen (HLA) matches with that of the patient and that the mortality rate before and after surgery of the donor whose HLA does not match with that of the patent is high. The gene therapy refers to a method in which a normal IDS gene is injected into the body using a viral or non-viral vector such as an adenovirus or a retrovirus. However, the gene therapy remains at an experimental level and is not yet clinically available.

Currently, the most widely used method is the enzyme replacement therapy (ERT) in which a recombinant IDS enzyme is administered to a patient. Normally, the patient visits the hospital once a week and is administered intravenously by professional medical staff. It takes 3 to 4 hours or longer for a single administration.

Patients suffering from Hunter syndrome have great limitations in everyday life because they have difficulties in catching objects or gait abnormality due to abnormalities of the joint system, or they often have developmental disorders, cognitive disorders, and behavior problems due to nervous system disorders. Therefore, the conventional intravenous infusion therapy, which involves frequent visits to the hospital and long treatment times, may lower the quality of life for the patients and their caregivers. More importantly, there is a problem that the therapeutic effect is significantly reduced due to the lowered compliance of the patents with the medication. Due to the characteristics of the conventional treatment method of supplementing IDS by an intravenous injection once a week, the concentration of IDS in the patient's body was the highest immediately after the intravenous injection, but gradually decreases over time, thereby increasing the concentration of GAG again in the body. An increase in the concentration of GAG leads to severe aggravation of the symptoms. Further, given the high severity and irreversibility of the symptoms of Hunter syndrome in general, if the patient misses the appropriate treatment period, the resulting aggravation of the symptoms can be very fatal and can greatly shorten the patient's life expectancy.

As discussed above, the intravenous administration of IDS in the conventional method for treating Hunter syndrome has the problem that the therapeutic effect is greatly restricted and the life expectancy of the patients can be shortened due to the lowered compliance of the patients with the medication. Therefore, there is a pressing demand for a new formulation and a treatment method to resolve the above-mentioned problem.

DISCLOSURE OF INVENTION

Technical Problem

An object of the present invention is to provide a formulation for treating Hunter syndrome, which is capable of enhancing the therapeutic convenience of the patient.

Another object of the present invention is to provide a formulation for treating Hunter syndrome, which can improve the patient's compliance with medication.

Solution to Problem

1. A formulation for treating Hunter syndrome, comprising a first composition for an intravenous injection and a second composition for a subcutaneous injection.
2. The formulation for treating Hunter syndrome according to Item 1 above, wherein the first composition is intravenously injected once every two months to twice a month, and the second composition is subcutaneously injected 1 to 7 times a week.
3. The formulation for treating Hunter syndrome according to Item 1 above, wherein the first composition is intravenously injected once a month, and the second composition is subcutaneously injected once a week.
4. The formulation for treating Hunter syndrome according to Item 1 above, wherein the first composition is injected at the first week of the month, and the second composition is injected 1 to 7 times per week from the next week to the last week.
5. The formulation for treating Hunter syndrome according to Item 1 above, wherein the first composition is injected at the first week of the two months, and the second composition is injected 1 to 7 times per week from the next week to the last week of the two months.
6. The formulation for treating Hunter syndrome according to Item 1 above, wherein the first composition comprises iduronate-2-sulfatase consisting of at least one of the amino acid sequences of SEQ ID NOS: 1 and 2.
7. The formulation for treating Hunter syndrome according to Item 1 above, wherein the second composition comprises iduronate-2-sulfatase consisting of at least one of the amino acid sequences of SEQ ID NOS: 1 and 2.

8. The formulation for treating Hunter syndrome according to Item 1 above, wherein the first composition is injected at an effective dose of 0.05 mg/kg to 20 mg/kg per week.
9. The formulation for treating Hunter syndrome according to Item 1 above, wherein the first composition is injected at an effective dose of 0.1 mg/kg to 5 mg/kg per week.
10. The formulation for treating Hunter syndrome according to Item 1 above, wherein the second composition is injected at an effective dose of 0.1 mg/kg to 40 mg/kg per week.
11. The formulation for treating Hunter syndrome according to Item 1 above, wherein the second composition is injected at an effective dose of 0.2 mg/kg to 10 mg/kg per week.
12. The formulation for treating Hunter syndrome according to Item 1 above, wherein the second composition comprises at least one buffer selected from the group consisting of sodium phosphate and L-histidine.
13. The formulation for treating Hunter syndrome according to Item 1 above, wherein the second composition comprises at least one stabilizer selected from the group consisting of Polysorbate 20 and arginine.
14. The formulation for treating Hunter syndrome according to Item 1 above, wherein the second composition comprises an absorption enhancer, which is hyaluronidase.
15. A method for treating Hunter syndrome, comprising intravenously injecting a first composition and subcutaneously injecting a second composition.
16. The method for treating Hunter syndrome according to Item 15 above, wherein the first composition is intravenously injected once every two months to twice a month, and the second composition is subcutaneously injected 1 to 7 times a week.
17. The method for treating Hunter syndrome according to Item 15 above, wherein the first composition is intravenously injected once a month, and the second composition is subcutaneously injected once a week.
18. The method for treating Hunter syndrome according to Item 15 above, wherein the first composition is injected at the first week of the month, and the second composition is injected 1 to 7 times per week from the next week to the last week.
19. The method for treating Hunter syndrome according to Item 15 above, wherein the first composition is injected at the first week of the two months, and the second composition is injected 1 to 7 times per week from the next week to the last week of the two months.
20. The method for treating Hunter syndrome according to Item 15 above, wherein the first composition comprises iduronate-2-sulfatase consisting of at least one of the amino acid sequences of SEQ ID NOS: 1 and 2.
21. The method for treating Hunter syndrome according to Item 15 above, wherein the second composition comprises iduronate-2-sulfatase consisting of at least one of the amino acid sequences of SEQ ID NOS: 1 and 2.
22. The method for treating Hunter syndrome according to Item 15 above, wherein the first composition is injected at an effective dose of 0.05 mg/kg to 20 mg/kg per week.
23. The method for treating Hunter syndrome according to Item 15 above, wherein the first composition is injected at an effective dose of 0.1 mg/kg to 5 mg/kg per week.
24. The method for treating Hunter syndrome according to Item 15 above, wherein the second composition is injected at an effective dose of 0.1 mg/kg to 40 mg/kg per week.
25. The method for treating Hunter syndrome according to Item 15 above, wherein the second composition is injected at an effective dose of 0.2 mg/kg to 10 mg/kg per week.
26. A formulation for treating Hunter syndrome, comprising a therapeutic composition subcutaneously administered to a patient at a dose of 0.001 mL/hour to 100 mL/hour.

Advantageous Effects of Invention

The therapeutic formulation and the therapeutic method of the present invention exhibit equivalent or better drug efficacy as compared with IV administration once a week.

The therapeutic formulation and the therapeutic method of the present invention exhibit equivalent or better drug efficacy as compared with the conventional IV administration once a week while reducing the number of visits of the patients suffering from Hunter syndrome to the hospital to twice a month or less.

The therapeutic formulation and the therapeutic method of the present invention can reduce the number of intravenous injections to the patients suffering from Hunter syndrome.

The therapeutic formulation and the therapeutic method of the present invention can improve the therapeutic convenience of the patients suffering from Hunter syndrome, who have difficulties in visiting the hospital.

The therapeutic formulation and the therapeutic method of the present invention improve the medication compliance of the patients suffering from Hunter syndrome with the medicine, thereby improving the therapeutic effect.

The therapeutic formulation and the therapeutic method of the present invention are suitable for effectively injecting iduronate-2-sulfatase consisting of a predetermined amino acid sequence.

The present invention can provide a formulation for treating Hunter syndrome, which improves its in vivo stability by comprising a buffer such as sodium phosphate and L-histidine in the second composition.

The present invention can provide a formulation for treating Hunter syndrome, which improves its storage and handling stability by comprising a stabilizer such as polysorbate 20 and arginine in the second composition.

The present invention can provide a formulation for treating Hunter syndrome, which has an improved absorption rate in the body by comprising an absorption enhancer such as hyaluronidase in the second composition.

BRIEF DESCRIPTION OF THE DRAWINGS

FIG. 1 shows the serum concentration of IDS with a single IV or SC administration of the formulation for treating Hunter syndrome in Test Example 1.

FIGS. 2(A) to 2(C) show the concentrations of GAG in the urine sample with a single IV or SC administration of the formulation for treating Hunter syndrome in Test Example 2.

FIG. 3 shows the concentration of GAG in the spleen sample with a single IV or SC administration of the formulation for treating Hunter syndrome in Test Example 2.

FIG. 4 shows the concentration of GAG in the heart sample with a single IV or SC administration of the formulation for treating Hunter syndrome in Test Example 2.

FIG. 5 shows the concentration of GAG in the kidney sample with a single IV or SC administration of the formulation for treating Hunter syndrome in Test Example 2.

FIG. 6 shows the concentration of GAG in the liver sample with a single IV or SC administration of the formulation for treating Hunter syndrome in Test Example 2.

FIG. 7 shows the concentration of GAG in the lung sample with a single IV or SC administration of the formulation for treating Hunter syndrome in Test Example 2.

FIG. 8 shows the concentration of GAG in the brain sample with a single IV or SC administration of the formulation for treating Hunter syndrome in Test Example 2.

FIG. 9 shows the concentration of GAG in the kidney sample with repeated and combined IV and SC administrations of the formulation for treating Hunter syndrome in Test Example 4.

FIG. 10 shows the concentration of GAG in the liver sample with repeated and combined IV and SC administrations of the formulation for treating Hunter syndrome in Test Example 4.

FIG. 11 shows the concentration of GAG in the spleen sample with repeated and combined IV and SC administrations of the formulation for treating Hunter syndrome in Test Example 4.

FIG. 12(A) to 12(C) show the concentrations of GAG in the urine sample with repeated and combined IV and SC administrations of the formulation for treating Hunter syndrome in Test Example 4.

MODE FOR CARRYING OUT THE INVENTION

The present invention relates to a formulation for treating Hunter syndrome and more specifically to a formulation for treating Hunter syndrome, which comprises a first composition for an intravenous injection and a second composition for a subcutaneous injection and is capable of exhibiting equivalent or better drug efficacy as compared with the conventional IV administration once a week while reducing the number of visits of the patients suffering from Hunter syndrome to the hospital to twice a month or less; improving the compliance of the patients suffering from Hunter syndrome with the medicine as compared with the conventional therapeutic formulation and method; and enhancing the welfare and convenience of the patients suffering from Hunter syndrome. The method of combined IV/SC administrations according to the present invention replaces a certain number of IV administrations in the conventional method of IV administration once a week, which requires that the patients visit the hospital every week, with SC administrations that can be made by the patents by themselves at home. The method of the present invention requires that the patents visit the hospital less often than the conventional method of IV administration once a week, while exhibiting equivalent or better drug efficacy as compared with the conventional IV administration once a week. Thus, the present invention starkly contradicts the conventional common idea that the therapeutic effect of SC administrations will not be superior to the therapeutic effect of IV administrations. Accordingly, the present invention relates to a formulation and a method, which drastically improve the therapeutic effect on Hunter syndrome as compared with the conventional therapy.

The present invention relates to a formulation for treating Hunter syndrome, which comprises a first composition for an intravenous injection and a second composition for a subcutaneous injection; and a method for treating Hunter syndrome, which comprises combined administrations of intravenously injecting a first composition and subcutaneously injecting a second composition.

Hereinafter, the present invention will be described in detail.

The formulation for treating Hunter syndrome according to the present invention comprises a first composition for an intravenous injection and a second composition for a subcutaneous injection.

The first composition is a composition for an intravenous injection. A composition for an intravenous injection refers to a sterile composition, which allows a drug in liquid phase to be injected directly into the vein to act. A composition for injection covers all compositions that can be used in the preparation of a customary injection and includes, but is not limited to, aqueous injections, non-aqueous injections, suspension injections, and freeze-dried injections.

The first composition is intravenously injected once every two months to twice a month.

The administration once a month means that the interval between the previous intravenous injection and the next intravenous injection is one month or so. For example, the interval between intravenous injections may be 25 days, 26 days, 27 days, 28 days, 29 days, 30 days, 31 days, 32 days, or 33 days, depending on the conditions of the patient or those of the treatment.

The first composition comprises an active ingredient that is effective in treating Hunter syndrome.

Iduronate-2-sulfatase (IDS or I2S) may be used as an active ingredient in the first composition.

IDS in the present invention comprises, for example, a protein consisting of the amino acid sequence of SEQ ID NO: 1 or 2. The protein consisting of the amino acid sequence of SEQ ID NO: 2 has the 59$^{th}$ cysteine (Cys) of the protein consisting of the amino acid sequence of SEQ ID NO: 1 substituted by formylglycine (FGly).

IDS comprises proteins in which some amino acids have been inserted, deleted, substituted, or the like, in the protein consisting of the amino acid sequence of SEQ ID NO: 1 or 2, as long as the therapeutic activity for treating Hunter syndrome is maintained.

IDS may be a protein derived from an animal such as a human or may be a recombinant protein.

IDS may be a mixture of two or more proteins. For example, IDS may be a mixture of a protein consisting of the amino acid sequence of SEQ ID NO: 1 and a protein consisting of the amino acid sequence of SEQ ID NO: 2. In addition, IDS may be, for example, a mixture of 35% (by mole) or less of a protein consisting of the amino acid sequence of SEQ ID NO: 1 and 65% or more, 70% or more, 75% or more, or 80% (by mole in each occurrence) or more of a protein consisting of the amino acid sequence of SEQ ID NO: 2.

If the protein consisting of the amino acid sequence of SEQ ID NO: 2 is contained in an amount of 65% (by mole) or more, the therapeutic effect on Hunter syndrome is improved.

The protein consisting of the amino acid sequence of SEQ ID NO: 1 or 2 may have mannose-6-phosphate (M6P) in an amount of 2.0 to 4.0 moles, preferably 2.3 to 3.5 moles, more preferably 2.5 to 3.0 moles, per 1 mole of the protein. Since M6P contributes to the uptake of IDS into the cells and the targeting of lysosomes, it is possible to effectively decompose glycosaminoglycan accumulated in the lysosomes if the content of M6P is high.

The first composition may comprise various inactive ingredients required for the intravenous injection composition other than the active ingredient (i.e., effective ingredient).

For example, the first composition may further comprise buffers (such as sodium phosphate and L-histidine), carbohydrates (such as glucose, mannose, sucrose, and dextran), stabilizers (such as sodium hydrogen sulfite, sodium sulfite or ascorbic acid, Polysorbate 20, and arginine), antioxidants, bacteriostatic agents, chelating agents (such as EDTA and glutathione), adjuvants (such as aluminum hydroxide), suspensions, thickeners, and/or preservatives (such as benzalkonium chloride, methyl- or propyl-paraben, and chlorobutanol). In addition, it may further comprise various antibacterial agents and antifungal agents such as parabens, chlorobutanol, phenol, sorbic acid, and thimerosal.

The first composition may comprise a liquid suitable for an intravenous injection. This liquid may be, but is not limited to, solvents or dispersion media comprising water, ethanol, polyols (such as glycerol, propylene glycol, and liquid polyethylene glycol), mixtures thereof and/or vegetable oils. More preferably, an isotonic solution such as saline, a Hanks' solution, a ringer solution, PBS (phosphate buffered saline) containing triethanolamine, or sterilized water for injection, 10% ethanol, 40% propylene glycol, and 5% dextrose may be used. In addition, Other liquids suitable for intravenous administration may also be referenced to Remington's Pharmaceutical Sciences, $19^{th}$ ed., Mack Publishing Company, Easton, Pa., 1995.

The second composition is a composition for a subcutaneous injection. A composition for a subcutaneous injection refers to a sterile composition, which allows a drug in liquid phase to be injected into the loose connective tissues below the dermis and absorbed through the capillary blood vessels to act.

The second composition is subcutaneously injected once to seven times a week.

The administration once to seven times a week means that the administration is performed at one time to seven times a week at regular intervals. For example, administration twice a week may be conducted on Monday and Thursday, on Tuesday and Friday, on Wednesday and Saturday, on Thursday and Sunday, on Friday and Monday, on Saturday and Tuesday, or on Sunday and Wednesday. Further, for example, administration three times a week may be performed on Monday, Wednesday, and Friday; on Tuesday, Thursday, and Saturday; on Wednesday, Friday, and Sunday; on Thursday, Saturday, and Monday; on Friday, Sunday, and Tuesday; or on Saturday, Monday, and Wednesday.

The second composition may be prepared basically by comprising components the same as, or similar to, those of the first composition (for example, the active ingredient (i.e., effective ingredient) and the inactive ingredients). These components may be changed for use as needed.

The second composition may comprise a liquid suitable for a subcutaneous injection. This liquid may be the same as, or similar to, that contained in the first composition and may be changed for use as needed.

The second composition may comprise sodium phosphate and L-histidine (20 mM, pH 6.0) as a buffer. The addition of a buffer can contribute to stabilization of the active pharmaceutical ingredient (API) in vivo even at a transient pH change.

The second composition may comprise Polysorbate 20 and arginine as a stabilizer. The concentration of Polysorbate 20 may be about 0.05 to 0.22 mg/mL.

Arginine may serve as a stabilizer and a solubilizer in addition to a buffer.

The second composition may comprise hyaluronidase as an absorption enhancer, which can enhance the absorption rate of the active ingredient in the body.

The second composition may comprise saline. The concentration of sodium chloride may be 2% or less, and the acidity (pH) may be from 3 to 8.

The order of injection of the first and second compositions may be such that the first composition is injected first, followed by injection of the second composition; or that the second composition is injected first, followed by injection of the first composition. For example, an intravenous injection may be administered at week 1, and subcutaneous injections may be administered at weeks 2 to 4; a subcutaneous injections may be administered at week 1, an intravenous injection may be administered at week 2, and subcutaneous injections may be administered at weeks 3 and 4; subcutaneous injections may be administered at weeks 1 and 2, an intravenous injection may be administered at week 3, and a subcutaneous injection may be administered at week 4; or subcutaneous injections may be administered at weeks 1-3 and an intravenous injection may be administered at week 4.

The first composition may be administered at various effective doses (i.e., the weight of the active ingredient administered per 1 kilogram of body weight to be treated in the unit of mg/kg or mpk) depending on the severity of the disease. Typically, it may be administered at an effect dose of 0.05 mg/kg to 20 mg/kg per week (for example, from 0.1 mg/kg to 5 mg/kg per week, from 0.5 mg/kg to 2 mg/kg per week, or from 0.5 mg/kg to 1 mg/kg per week). According to a more specific example, it may be administered at an effective dose of 0.5 mg/kg per week.

The second composition may be administered at various effective doses depending on the severity of the disease. Typically, it may be administered at an effect dose of 0.1 mg/kg to 40 mg/kg per week (for example, from 0.2 mg/kg to 20 mg/kg per week, from 0.5 mg/kg to 10 mg/kg per week, or from 0.5 mg/kg to 5 mg/kg per week). According to a more specific example, it may be administered at an effective dose of 1 mg/kg to 5 mg/kg per week (for example, from 2.5 mg/kg to 5 mg/kg per week). Also, the single dose volume of the second composition may be 2 mL/site or less (for example, 1 mL/site or less), and the concentration of IDS may be 1 to 300 mg/mL.

The weekly dose of the second composition may be such that the concentration of IDS in the patient's serum is 10 to 10,000 ng/mL within 24 hours after administration; that the average maximum serum concentration ($C_{max}$) is 1.5 μg/mL or more; and that the area under the concentration-time curve (AUC) is 200 to 1,000 min* μg/mL or more.

The administration of the second composition may be such that IDS is delivered to tissues selected from the group consisting of muscle, skin, liver, kidney, spleen, joint, bone, lung, airway, tongue, upper respiratory tract, eye, ear, connective tissue, and heart; or that the concentration of IDS in the above-mentioned tissues may be increased. The administration of the second composition may cause the activity of IDS in the tissues to increase by at least 1 to 10 folds or more of the control group; that the increased activity is 10 to 600 nmole/hr/mg or more; and that the increased activity is 10 to 95% or more of the normal IDS activity.

The administration of the second composition may be such that the concentration of GAG in the serum, plasma, urine, and above-mentioned tissues is reduced by 10 to 100% of the difference in the concentration of GAG between the control group (i.e., control group before administration or untreated) and the normal group (i.e., normal tissues that are not affected by Hunter syndrome); and that the size of the liver or spleen may be reduced by 10 to 100% of the difference in size between the control group (i.e., control group before administration or untreated) and the normal group (i.e., normal tissues that are not affected by Hunter syndrome).

The administration of the second composition may be such that the result in a 6-minute gait test is improved by 10 to 250 meters or more over the control group (i.e., control group before administration or untreated) and by 10 to 1,000% or more over the control group (i.e., control group before administration or untreated).

Hereinafter, the present invention will be described in more detail with reference to the following examples and test examples. However, these examples and test examples are set forth to illustrate the present invention in detail, and the scope of the present invention is not limited thereto.

In the following test examples, IV or I.V stands for intravenous injection. SC or S.C stands for subcutaneous injection. PK refers to pharmacokinetics. PD stands for pharmacodynamics. Also, WT stands for wild-type, and KO stands for IDS knock-out.

TEST EXAMPLE 1

Pharmacokinetic Study on the Treatment of Hunter Syndrome with a Single IV or SC Administration An IV composition and an SC composition were administered to mice to measure the serum concentration of IDS, and such pharmacokinetic analysis as AUC and bioavailability were carried out. Here, 6 to 8-week-old male mice were used. The experiment design is summarized in Table 1.

TABLE 1

Pharmacokinetic experiment design with single administration

| Group (start age) | Subgroup (3/time point) | Route | Dosing Regimen (mg/kg) | PK time points |
|---|---|---|---|---|
| WT male (n = 72) (6-8-week-old) | N = 18 | I.V | 5 | 5 min, 30 min, 1 hr, 3 hr, 6 hr, 8 hr |
| | N = 18 | S.C | 5 | 1 hr, 2 hr, 8 hr, 12 hr, 16 hr, 24 hr |
| | N = 18 | S.C | 10 | 1 hr, 2 hr, 8 hr, 12 hr, 16 hr, 24 hr |
| | N = 18 | S.C | 20 | 1 hr, 2 hr, 8 hr, 12 hr, 16 hr, 24 hr |

Seventy-two normal mice were divided into four groups. One group was administered with an intravenous injection of 5 mg/kg corresponding to 10 times the clinical dose (0.5 mg/kg) of an intravenous injection (IV), and the other three groups were administered with a subcutaneous injection of 5, 10, and 20 mg/kg, respectively. The serum concentration of IDS was analyzed by ELISA. The results are shown in FIG. 1. PHOENIX™ WINNONLIN® (ver 6.4, Pharsight)/NCA (non-compartmental analysis) was used for the PK analysis. The results of pharmacokinetic analysis are summarized in Table 2.

TABLE 2

Results of pharmacokinetic analysis with single administration

| PK parameters | Intravenous injection 5 mg/kg | Subcutaneous injection 5 mg/kg | 10 mg/kg | 20 mg/kg |
|---|---|---|---|---|
| $C_{max}$ (μg/mL) | 66.8 ± 1.57 | 1.41 ± 0.30 | 2.90 ± 0.687 | 8.48 ± 1.27 |
| $C_{max}/D$ (kg · μg/mL/mg) | — | 0.281 ± 0.06 | 0.290 ± 0.0687 | 0.424 ± 0.0636 |
| $C_0$ (μg/mL) | 82.4 ± 1.28 | — | — | — |
| $C_{last}$ (μg/mL) | 0.176 ± 0.0187 | 0.116 ± 0.002 | 0.113 ± 0.0474 | 0.393 ± 0.0459 |
| $T_{max}$ (hr) | — | 1.00 ± 0.00 | 1.00 ± 0.00 | 1.00 ± 0.00 |
| $T_{1/2}$ (hr, terminal phase) | 1.80 ± 0.218 | 6.89 ± 0.952 | 5.25 ± 0.501 | 5.60 ± 0.567 |
| $AUC_{INF}$ (hr · μg/mL) | 48.2 ± 3.61 | 10.6 ± 0.958 | 19.2 ± 4.02 | 53.9 ± 0.444 |
| $AUC_{INF}/D$ (hr · kg · μg/mL/mg) | — | 2.12 ± 0.192 | 1.92 ± 0.402 | 2.69 ± 0.0222 |
| AUC %_Extrap (%) | 0.969 ± 0.279 | 11.0 ± 2.24 | 4.37 ± 1.39 | 5.94 ± 1.27 |
| Cl (mL/hr/kg) | 104.1 ± 7.97 | — | — | — |
| Vss (mL/kg) | 83.3 ± 3.99 | — | — | — |
| $MRT_{INF}$ (hr) | 0.801 ± 0.0235 | 10.0 ± 1.16 | 7.29 ± 0.362 | 7.52 ± 0.765 |
| BA (%) | — | 22.0 | 19.9 | 27.9 |

As shown in the table above, IDS reached the maximum serum concentration ($C_{max}$, μg/mL) at a rapid rate within 1 hour in the case of SC administration. The half-life ($T_{1/2}$, hr) was 1.80 hr in the terminal phase in the case of IV administration, whereas the half-life was increased to 5.25 to 6.89 hr in the case of SC administration. The mean retention time (MRT, hr) was 0.801 hr in the group administered with an IV injection and 7.29 to 10.0 hr in the group administered with an SC injection. The concentration ($C_0$, μg/mL) immediately after an IV administration was 82.4 μg/mL, which confirmed that most of the dose (5 mg/kg) was recovered. The $C_{max}$ and $AUC_{INF}$ values, which show the body's exposure to drugs upon an SC administration, increased dose-dependently. However, the increase was slightly greater in the group administered with 20 mg/kg than in the groups administered with 5 and 10 mg/kg. The AUC %_Extrap value was 0.969 to 11.0% in all treatment groups.

The bioavailability (BA, %) values were 22.0%, 19.9%, and 27.9% in the groups SC administered with 5, 10, and 20 mg/kg (with reference to AUC when 5 mg/kg was SC administered and with an assumption of linear PK), respectively. Overall, the BA values were approximately 20% when compared with the case of an IV administration. Therefore, it is expected that an SC administration at a dose of approximately 5 times (2.5 mg/kg) the IV dose will show a similar therapeutic effect to that of an IV administration.

TEST EXAMPLE 2

Pharmacodynamic Study on the Treatment of Hunter Syndrome with a Single IV or SC Administration In consideration of the pharmacokinetic analysis (i.e., the BA value of an SC injection was about 20% of that of an IV injection), the effective dose of an SC injection was set to 2.5 mg/kg. After a single IV or SC injection, the effect thereof on reduction in the concentration of GAG was compared for 4 weeks. Urine samples were collected on the last day of Week 2 (i.e., Day 14) and on the last day of Week 4 (i.e., Day 28) counting from the day of dosing (Day 0). Samples of tissues (liver, brain, heart, kidney, spleen, and lung) were also collected on the last day of Week 4 (i.e., Day 28) for the measurement of GAG concentrations. A urine samples was collected once for three days prior to the drug administration for comparison. The pharmacodynamic experiment design is summarized in Table 3.

TABLE 3

Pharmacodynamic experiment design with single administration

| Group (start age) | Test item | Subgroup | Route | Dosing Regimen (mg/kg) |
|---|---|---|---|---|
| WT (n = 6) | Vehicle | N = 6 | S.C | — |
| KO (n = 30) | Vehicle | N = 6 | S.C | — |
| (6-8-week-old) | Formulation for treating Hunter syndrome | N = 6 | S.C | 0.5 |
| | | N = 6 | S.C | 2.5 |
| | | N = 6 | S.C | 12.5 |
| | Formulation for treating Hunter syndrome | N = 6 | I.V | 0.5 |

The results of GAG concentration analysis of the urine samples according to the experiment design shown in Table 3 are summarized in Table 4 and FIGS. 2(A), 2(B), and 2(C).

TABLE 4

Results of GAG concentration analysis of the urine samples with single administration (Day 28)

| Group | | GAG (μg/μg of creatinine) | P-value | Summary |
|---|---|---|---|---|
| WT (n = 6) | | 0.577 ± 0.155 | <0.001 | *** |
| KO (n = 6) | | 1.29 ± 0.0958 | — | — |
| SC | 0.5 mg/kg (n = 6) | 1.07 ± 0.0975 | <0.05 | * |
| | 2.5 mg/kg (n = 6) | 0.867 ± 0.101 | <0.001 | *** |
| | 12.5 mg/kg (n = 6) | 0.815 ± 0.113 | <0.001 | *** |
| IV | 0.5 mg/kg (n = 6) | 0.923 ± 0.136 | <0.001 | *** |

The GAG concentration values were expressed as Mean ± SEM.
* $p < 0.05$,
** $p < 0.01$,
*** $p < 0.001$ vs KO.
One-way ANOVA and Dunnett's Multiple Comparison Test (GraphPad Prism)

The results of GAG concentration analysis of the spleen samples according to the experiment design shown in Table 3 are summarized in Table 5 and FIG. 3.

TABLE 5

Results of GAG concentration analysis of the spleen samples with single administration (Day 28)

| Group | | GAG (μg/mg of protein) | P-value | Summary |
|---|---|---|---|---|
| WT (n = 6) | | 1.41 ± 0.121 | <0.001 | *** |
| KO (n = 6) | | 8.55 ± 0.619 | — | — |
| SC | 0.5 mg/kg (n = 6) | 5.88 ± 0.329 | <0.001 | *** |
| | 2.5 mg/kg (n = 6) | 5.89 ± 0.524 | <0.001 | *** |
| | 12.5 mg/kg (n = 6) | 4.03 ± 0.362 | <0.001 | *** |
| IV | 0.5 mg/kg (n = 6) | 4.80 ± 0.470 | <0.001 | *** |

The GAG concentration values were expressed as Mean ± SEM.
* $p < 0.05$,
** $p < 0.01$,
*** $p < 0.001$ vs KO.
One-way ANOVA and Dunnett's Multiple Comparison Test (GraphPad Prism)

The results of GAG concentration analysis of the heart samples according to the experiment design shown in Table 3 are summarized in Table 6 and FIG. 4.

TABLE 6

Results of GAG concentration analysis of the heart samples with single administration (Day 28)

| Group | | GAG (μg/mg of protein) | P-value | Summary |
|---|---|---|---|---|
| WT (n = 6) | | 0.390 ± 0.0594 | <0.001 | ### |
| KO (n = 6) | | 11.1 ± 0.560 | — | — |
| SC | 0.5 mg/kg (n = 6) | 10.7 ± 0.799 | >0.05 | — |
| | 2.5 mg/kg (n = 6) | 6.75 ± 0.405 | >0.05 | — |
| | 12.5 mg/kg (n = 6) | 3.49 ± 0.212 | <0.01 | ## |
| IV | 0.5 mg/kg (n = 6) | 5.96 ± 0.0613 | >0.05 | — |

The GAG concentration values were expressed as Mean ± SEM.
: $p < 0.05$,
: $p < 0.01$,
: $p < 0.001$ vs KO.
Kruskal-Wallis Test and Dunn's Multiple Comparison Test (GraphPad Prism)

The results of GAG concentration analysis of the kidney samples according to the experiment design shown in Table 3 are summarized in Table 7 and FIG. 5.

TABLE 7

Results of GAG concentration analysis of the kidney samples with single administration (Day 28)

| Group | | GAG (μg/mg of protein) | P-value | Summary |
|---|---|---|---|---|
| WT (n = 6) | | 0.639 ± 0.0593 | <0.01 | ## |
| KO (n = 6) | | 25.0 ± 0.957 | — | — |
| SC | 0.5 mg/kg (n = 6) | 25.9 ± 0.645 | >0.05 | — |
| | 2.5 mg/kg (n = 6) | 23.8 ± 0.821 | >0.05 | — |
| | 12.5 mg/kg (n = 6) | 16.4 ± 0.740 | >0.05 | — |
| IV | 0.5 mg/kg (n = 6) | 23.5 ± 1.34 | >0.05 | — |

The GAG concentration values were expressed as Mean ± SEM.
: $p < 0.05$,
: $p < 0.01$,
: $p < 0.001$ vs KO.
Kruskal-Wallis Test and Dunn's Multiple Comparison Test (GraphPad Prism)

The results of GAG concentration analysis of the liver samples according to the experiment design shown in Table 3 are summarized in Table 8 and FIG. 6.

TABLE 8

Results of GAG concentration analysis of the liver
samples with single administration (Day 28)

| Group | | GAG (μg/mg of protein) | P-value | Summary |
|---|---|---|---|---|
| WT (n = 6) | | 0.676 ± 0.0143 | <0.001 | ### |
| KO (n = 6) | | 50.5 ± 1.19 | — | — |
| SC | 0.5 mg/kg (n = 6) | 23.7 ± 0.159 | >0.05 | — |
|  | 2.5 mg/kg (n = 6) | 18.6 ± 0.815 | >0.05 | — |
|  | 12.5 mg/kg (n = 6) | 10.3 ± 0.799 | <0.01 | ## |
| IV | 0.5 mg/kg (n = 6) | 16.0 ± 0.762 | >0.05 | — |

The GAG concentration values were expressed as Mean ± SEM.
\#: $p < 0.05$,
\##: $p < 0.01$,
\###: $p < 0.001$ vs KO.
Kruskal-Wallis Test and Dunn's Multiple Comparison Test (GraphPad Prism)

The results of GAG concentration analysis of the lung samples according to the experiment design shown in Table 3 are summarized in Table 9 and FIG. 7.

TABLE 9

Results of GAG concentration analysis of the lung
samples with single administration (Day 28)

| Group | | GAG (μg/mg of protein) | P-value | Summary |
|---|---|---|---|---|
| WT (n = 6) | | 0.992 ± 0.0951 | <0.001 | ### |
| KO (n = 6) | | 34.4 ± 2.43 | — | — |
| SC | 0.5 mg/kg (n = 6) | 31.3 ± 2.42 | >0.05 | — |
|  | 2.5 mg/kg (n = 6) | 28.8 ± 2.10 | >0.05 | — |
|  | 12.5 mg/kg (n = 6) | 19.2 ± 0.955 | <0.05 | # |
| IV | 0.5 mg/kg (n = 6) | 29.1 ± 2.11 | >0.05 | — |

The GAG concentration values were expressed as Mean ± SEM.
\#: $p < 0.05$,
\##: $p < 0.01$,
\###: $p < 0.001$ vs KO.
Kruskal-Wallis Test and Dunn's Multiple Comparison Test (GraphPad Prism)

The results of GAG concentration analysis of the brain samples according to the experiment design shown in Table 3 are summarized in Table 10 and FIG. 8.

TABLE 10

Results of GAG concentration analysis of the brain
samples with single administration (Day 28)

| Group | | GAG (μg/mg of protein) | P-value | Summary |
|---|---|---|---|---|
| WT (n = 6) | | 0.558 ± 0.0369 | <0.001 | *** |
| KO (n = 6) | | 1.27 ± 0.0651 | — | — |
| SC | 0.5 mg/kg (n = 6) | 1.27 ± 0.0868 | >0.05 | — |
|  | 2.5 mg/kg (n = 6) | 1.19 ± 0.0602 | >0.05 | — |
|  | 12.5 mg/kg (n = 6) | 1.16 ± 0.0756 | >0.05 | — |
| IV | 0.5 mg/kg (n = 6) | 1.12 ± 0.0798 | >0.05 | — |

The GAG concentration values were expressed as Mean ± SEM.
\* $p < 0.05$,
\** $p < 0.01$,
\*** $p < 0.001$ vs KO.
One-way ANOVA and Dunnett's Multiple Comparison Test (GraphPad Prism)

Taking all the results shown in Tables 4 to 10 into consideration, it can be seen that the formulation for treating Hunter syndrome of the present invention generally exhibits the effect of reducing GAG dose-dependently when administered by a single subcutaneous (SC) injection. Further, when 2.5 mg/kg is administered by a subcutaneous (SC) injection, the effect of reducing GAG is similar to that of the clinical dose of 0.5 mg/kg of an intravenous (IV) injection.

TEST EXAMPLE 3

Determination of SC Infusion Rate of the Formulation for Treating Hunter Syndrome A commercially marketed vial for an intravenous injection of IDS has a size of 3.0 mL, which contains a solution that comprises 6.0 mg of an IDS enzyme in a concentration of 2.0 mg/mL. This medicine is for one-time use. The recommended dose to the patients is 0.5 mg per 1 kg of the body weight, which is gradually administered to the patients intravenously when the patient visits the hospital once a week. The amount corresponding to the patient's body weight is diluted in 100 mL of 0.9% sodium chloride water for injection, which is administered intravenously. The total dose should be gradually administered over 1 to 3 hours or longer. The infusion time may be extended due to any infusion related reactions. However, the infusion time should not exceed 8 hours. The initial infusion rate should be 8 mL/hour for 15 minutes from the beginning of infusion, and the infusion rate may then be increased by 8 mL/hour at 15-minute intervals to allow the total dose to be administered within the expected time if no toxicity appears. However, doctors and nurses are instructed that the infusion rate should not exceed a maximum of 100 mL/hour.

For a subcutaneous injection, a relatively small volume is generally administered at once. However, a drug may be administered in a continuous SC or SC infusion if there is a limit that the drug is concentrated to reduce the total volume of the drug. In the case where a drug originally developed for an intravenous injection is changed for a subcutaneous injection as in the present invention, whether the drug is suitable for a continuous SC or SC infusion should be clearly confirmed. According to the present invention, a subcutaneous administration may be carried out at a volume of 2 mL/site or less. According to a more specific example, the dosage may be 1 mL/site or less.

TEST EXAMPLE 4

Pharmacodynamic Study on the Treatment of Hunter Syndrome with Repeated and Combined IV and SC Administrations The active ingredient of Idursulfase beta according to one embodiment of the present invention was used. The effective dose for IV was 0.5 mg/kg, and the effective dose for SC was 0.5 mg/kg, 1 mg/kg, 2.5 mg/kg, or 5 mg/kg. Mice were subjected to repeated IV administrations, repeated SC administrations, and repeated IV and SC administrations in accordance with the experiment design as shown in Table 11 below. In the case where the effective dose for IV and SC is 0 mg/kg in Table 11, it means a control group in which only saline was administered.

TABLE 11

| Mouse | Substance | Weekly dosing scheme | | | | | | | |
|---|---|---|---|---|---|---|---|---|---|
| | | Day 0 | Day 7 | Day 14 | Day 21 | Day 28 | Day 35 | Day 42 | Day 49 |
| WT | Saline | IV (0) | SC (0) | SC (0) | SC (0) | IV (0) | SC (0) | SC (0) | SC (0) |
| IDS KO | Saline | IV (0) | SC (0) | SC (0) | SC (0) | IV (0) | SC (0) | SC (0) | SC (0) |
| | Idursulfase beta | IV (0.5) | SC (0.5) | SC (0.5) | SC (0.5) | IV (0.5) | SC (0.5) | SC (0.5) | SC (0.5) |
| | | IV (0.5) | SC (1) | SC (1) | SC (1) | IV (0.5) | SC (1) | SC (1) | SC (1) |
| | | IV (0.5) | SC (2.5) | SC (2.5) | SC (2.5) | IV (0.5) | SC (2.5) | SC (2.5) | SC (2.5) |
| | | IV (0.5) | SC (5) | SC (5) | SC (5) | IV (0.5) | SC (5) | SC (5) | SC (5) |
| | | IV (0.5) | IV (0.5) | IV (0.5) | IV (0.5) | IV (0.5) | IV (0.5) | IV (0.5) | IV (0.5) |
| | | SC (2.5) | SC (2.5) | SC (2.5) | SC (2.5) | SC (2.5) | SC (2.5) | S (2.5) | SC (2.5) |
| | Idursulfase | IV (0.5) | IV (0.5) | IV (0.5) | IV (0.5) | IV (0.5) | IV (0.5) | IV (0.5) | IV (0.5) |

\* Day 0 refers to the first administration day, and Day 7, Day 14, Day 21, Day 28, Day 35, Day 42, and Day 49 refer to the $7^{th}$, $14^{th}$, $21^{st}$, $28^{th}$, $35^{th}$, $42^{nd}$, and $49^{th}$ days from the first administration day, respectively.
\* Urine samples were collected on Day −3, Day 14, Day 28, and Day 56; and Day −3 refers to 3 days before the first administration day.
\* Tissue samples were collected on Day 56.
\* IV or SC stands for the administration route on the corresponding administration day (IV: intravenous injection, SC: subcutaneous injection).
\* The number in parentheses after IV or SC indicates the effective dose of the formulation for treating Hunter syndrome per administration in the unit of mg/kg.
\* Idursulfase beta is the active ingredient according to one embodiment of the present invention.
\* Idursulfase was used as a control group.

In accordance with the above experiment design, repeated IV administrations, repeated SC administrations, and repeated IV and SC administrations were carried out in a total of 8 times in each test at intervals of one week. Urine samples were collected on three days before the first administration day, the $14^{th}$ day, $28^{th}$ day, and $56^{th}$ day from the first administration day, respectively. Tissue samples were collected on the $56^{th}$ day (D 56). The effect of reducing GAG was then compared.

The results of GAG concentration analysis of the kidney, liver, and spleen samples according to the experiment design shown in Table 11 are summarized in Tables 12 to 14 and FIGS. 9 to 11.

As shown in Table 12 and FIG. 9, when the formulation for treating Hunter syndrome was administered in combination of an effective IV dose of 0.5 mg/kg and an effective SC dose of 2.5 mg/kg (see "0.5 IV→2.5 SC" in Table 12 and FIG. 9) and when the formulation for treating Hunter syndrome was administered in combination of an effective IV dose of 0.5 mg/kg and an effective SC dose of 5.0 mg/kg (see "0.5 IV →5.0 SC" in Table 12 and FIG. 9), the concentrations of GAG in the kidney were equivalent to, or lower than, that of the repeated administrations of the formulation at an effective IV dose of 0.5 mg/kg (see "0.5 IV" in Table 12 and FIG. 9).

TABLE 12

Results of GAG concentration analysis of the kidney samples with combined administrations (Day 56)

| Mouse | Substance | Concentration | GAG (μg/mg of protein) | P-value | Summary |
|---|---|---|---|---|---|
| WT (n = 4) | Saline | — | 0.25 ± 0.25 | <0.001 | *** |
| IDS KO (n = 4) | Saline | — | 20.65 ± 0.30 | — | — |
| | Idursulfase beta | 0.5 IV → 0.5 SC | 13.66 ± 1.40 | <0.05 | * |
| | | 0.5 IV → 1.0 SC | 13.98 ± 0.94 | <0.05 | * |
| | | 0.5 IV → 2.5 SC | 10.86 ± 1.22 | <0.01 | ** |
| | | 0.5 IV → 5.0 SC | 6.61 ± 2.66 | <0.001 | *** |
| | | 2.5 SC | 14.83 ± 0.90 | >0.05 | — |
| | | 0.5 IV | 8.01 ± 2.92 | <0.001 | *** |
| | Idursulfase | 0.5 IV | 10.47 ± 1.92 | <0.001 | *** |

The GAG concentration values were expressed as Mean ± SEM.
\* $p < 0.05$,
\*\* $p < 0.01$,
\*\*\* $p < 0.001$ vs KO.
One-way ANOVA and Dunnett's Multiple Comparison Test (GraphPad Prism)

TABLE 13

Results of GAG concentration analysis of the liver samples with combined administrations (Day 56)

| Mouse | Substance | Concentration | GAG (μg/mg of protein) | P-value | Summary |
|---|---|---|---|---|---|
| WT (n = 4) | Saline | — | 0.94 ± 0.09 | <0.001 | *** |
| IDS KO (n = 4) | Saline | — | 30.05 ± 0.65 | — | — |
| | Idursulfase beta | 0.5 IV → 0.5 SC | 1.60 ± 0.43 | <0.001 | *** |
| | | 0.5 IV → 1.0 SC | 1.31 ± 0.38 | <0.001 | *** |
| | | 0.5 IV → 2.5 SC | 1.58 ± 0.42 | <0.001 | *** |
| | | 0.5 IV → 5.0 SC | 0.81 ± 0.18 | <0.001 | *** |
| | | 2.5 SC | 2.75 ± 0.66 | <0.001 | *** |
| | | 0.5 IV | 0.91 ± 0.17 | <0.001 | *** |
| | Idursulfase | 0.5 IV | 1.07 ± 0.21 | <0.001 | *** |

The GAG concentration values were expressed as Mean ± SEM.
\* $p < 0.05$,
\*\* $p < 0.01$,
\*\*\* $p < 0.001$ vs KO.
One-way ANOVA and Dunnett's Multiple Comparison Test (GraphPad Prism)

As shown in Table 13 and FIG. 10, when the formulation for treating Hunter syndrome was administered in combination of an effective IV dose of 0.5 mg/kg and an effective SC dose of 0.5 mg/kg (see "0.5 IV→0.5 SC" in Table 13 and FIG. 10), when the formulation for treating Hunter syndrome was administered in combination of an effective IV dose of 0.5 mg/kg and an effective SC dose of 1.0 mg/kg (see "0.5 IV→1.0 SC" in Table 13 and FIG. 10), when the formulation for treating Hunter syndrome was administered in combination of an effective IV dose of 0.5 mg/kg and an effective SC dose of 2.5 mg/kg (see "0.5 IV→2.5 SC" in Table 13 and FIG. 10), and when the formulation for treating Hunter syndrome was administered in combination of an effective IV dose of 0.5 mg/kg and an effective SC dose of 5.0 mg/kg (see "0.5 IV→5.0 SC" in Table 13 and FIG. 10), the concentrations of GAG in the liver were equivalent to, or lower than, that of the repeated administrations of the formulation at an effective IV dose of 0.5 mg/kg (see "0.5 IV" in Table 13 and FIG. 10).

TABLE 14

Results of GAG concentration analysis of the spleen samples with combined administrations (Day 56)

| Mouse | Substance | Concentration | GAG (μg/mg of protein) | P-value | Summary |
|---|---|---|---|---|---|
| WT (n = 4) | Saline | — | 0.00 ± 0.00 | <0.001 | *** |
| IDS KO (n = 4) | Saline | — | 4.64 ± 0.43 | — | — |
| | Idursulfase beta | 0.5 IV → 0.5 SC | 1.20 ± 0.44 | <0.001 | *** |
| | | 0.5 IV → 1.0 SC | 0.77 ± 0.27 | <0.001 | *** |
| | | 0.5 IV → 2.5 SC | 0.85 ± 0.53 | <0.001 | *** |
| | | 0.5 IV → 5.0 SC | 0.45 ± 0.27 | <0.001 | *** |
| | | 2.5 SC | 1.43 ± 0.15 | <0.001 | *** |
| | | 0.5 IV | 0.68 ± 0.31 | <0.001 | *** |
| | Idursulfase | 0.5 IV | 0.65 ± 0.23 | <0.001 | *** |

The GAG concentration values were expressed as Mean ± SEM.
* $p < 0.05$,
** $p < 0.01$,
*** $p < 0.001$ vs KO.
One-way ANOVA and Dunnett's Multiple Comparison Test (GraphPad Prism)

As shown in Table 14 and FIG. 11, when the formulation for treating Hunter syndrome was administered in combination of an effective IV dose of 0.5 mg/kg and an effective SC dose of 1.0 mg/kg (see "0.5 IV→1.0 SC" in Table 14 and FIG. 11), when the formulation for treating Hunter syndrome was administered in combination of an effective IV dose of 0.5 mg/kg and an effective SC dose of 2.5 mg/kg (see "0.5 IV→2.5 SC" in Table 14 and FIG. 11), and when the formulation for treating Hunter syndrome was administered in combination of an effective IV dose of 0.5 mg/kg and an effective SC dose of 5.0 mg/kg (see "0.5 IV→5.0 SC" in Table 14 and FIG. 11), the concentrations of GAG in the spleen were equivalent to, or lower than, that of the repeated administrations of the formulation at an effective IV dose of 0.5 mg/kg (see "0.5 IV" in Table 14 and FIG. 11).

In accordance with the experiment design shown in Table 11, urine samples were collected on Day 0, Day 14, Day 28, and Day 56. The results of GAG concentration analysis are summarized in Table 15 and FIGS. 12(A), 12(B), and 12(C).

TABLE 15

Results of GAG concentration analysis of the urine samples with combined administrations (Day 56)

| Mouse | Substance | Concentration | GAG (μg/mg of protein) | P-value | Summary |
|---|---|---|---|---|---|
| WT (n = 4) | Saline | — | 0.14 ± 0.02 | <0.01 | ** |
| IDS KO (n = 4) | Saline | — | 0.49 ± 0.04 | — | — |
| | Idursulfase beta | 0.5 IV → 0.5 SC | 0.27 ± 0.06 | >0.05 | — |
| | | 0.5 IV → 1.0 SC | 0.26 ± 0.07 | <0.05 | * |
| | | 0.5 IV → 2.5 SC | 0.31 ± 0.06 | >0.05 | — |
| | | 0.5 IV → 5.0 SC | 0.24 ± 0.02 | <0.05 | * |
| | | 2.5 SC | 0.39 ± 0.09 | >0.05 | — |
| | | 0.5 IV | 0.32 ± 0.01 | >0.05 | — |
| | Idursulfase | 0.5 IV | 0.25 ± 0.03 | <0.05 | * |

The GAG concentration values were expressed as Mean ± SEM.
* $p < 0.05$,
** $p < 0.01$,
*** $p < 0.001$ vs KO.
One-way ANOVA and Dunnett's Multiple Comparison Test (GraphPad Prism)

As shown in Table 15 and FIGS. 12(A),12(B), and 12(C), when the formulation for treating Hunter syndrome was administered in combination of an effective IV dose of 0.5 mg/kg and an effective SC dose of 1.0 mg/kg (see "0.5 IV→1.0 SC" in Table 15 and FIGS. 12(A), 12(B), and 12(C)), when the formulation for treating Hunter syndrome was administered in combination of an effective IV dose of 0.5 mg/kg and an effective SC dose of 2.5 mg/kg (see "0.5 IV→2.5 SC" in Table 15 and FIGS. 12(A), 12(B), and 12(C)), and when the formulation for treating Hunter syndrome was administered in combination of an effective IV dose of 0.5 mg/kg and an effective SC dose of 5.0 mg/kg (see "0.5 IV→5.0 SC" in Table 15 and FIGS. 12(A), 12(B), and 12(C)), the concentrations of GAG in all of the urine samples collected on Day 14, Day 28, and Day 56 were equivalent to, or lower than, that of the repeated administrations of the formulation at an effective IV dose of 0.5 mg/kg (see "0.5 IV" in Table 15 and FIGS. 12(A), 12(B), and 12(C)).

Taking into consideration all the results of experiments conducted in accordance with the experiment design shown in Table 11, it can be seen that the method of combined IV/SC administrations according to the present invention, particularly the combined administrations of an effective IV dose of 0.5 mg/kg and an effective SC dose of 2.5 mg/kg to 5 mg/kg, had an effect in treating Hunter syndrome equivalent to, or better than, that of the conventional IV administration (i.e., IV administrations at intervals of 7 days).

Therefore, the formulation for combined IV/SC administrations and the method of combined IV/SC administrations according to the present invention replace a certain number of IV administrations in the conventional method of IV administration once a week, which requires that the patients visit the hospital every week and takes 3 to 4 hours or longer per administration, with SC administrations that can be made by the patents by themselves at home. The formulation and the method of the present invention require that the patents visit the hospital less often than the conventional method of IV administration once a week, thereby eliminating the chances that the patients fail to visit the hospital for treatment, which drastically improves the compliance of the patients suffering from Hunter syndrome with the medicine. In addition, since the formulation and the method of the present invention exhibit drug efficacy equivalent to, or better than, that of the conventional IV administration once a week, it is possible to treat Hunter syndrome more effectively as compared with the conventional therapy.

TEST EXAMPLE 5

Active Ingredient of the Formulation for Treating Hunter Syndrome

The active ingredient that can be employed in the formulation and the method for treating Hunter syndrome according to an embodiment of the present invention may comprise, for example, SEQ ID NO: 1 and SEQ ID NO: 2.

| Sequence Listing Free Text |
| --- |
| SEQ. ID NO: 1<br>IDS amino acid sequence<br>525 a.a.<br>SETQANSTTD ALNVLLIIVD DLRPSLGCYG DKLVRSPNID<br>QLASHSLLFQ NAFAQQAVCA PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDPEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW |

| Sequence Listing Free Text |
| --- |
| AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMP |
| SEQ. ID NO: 2<br>IDS amino acid sequence<br>525 a.a.<br>SETQANSTTD ALNVLLIIVD DLRPSLGCYG DKLVRSPNID<br>QLASHSLLFQ NAFAQQAVG*A PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDPEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMP |

(G* at position 59 of SEQ ID NO: 2 above refers to formlglycine (FGly).

The invention claimed is:

1. A method for treating Hunter syndrome in a subject in need thereof, comprising administrating a first composition and administrating a second composition, to the subject,
   wherein the first composition comprising iduronate-2-sulfatase consisting of at least one of the amino acids sequences of SEQ ID NO: 1 and 2, and is administered by intravenous injection as a first administration during a first week of administration, and
   wherein the second composition comprising iduronate-2-sulfatase consisting of at least one of the amino acids sequences of SEQ ID NO: 1 and 2, and is administered by subcutaneous injection as subsequent administrations during second, third, and fourth weeks of administration.

2. The method for treating Hunter syndrome according to claim 1, wherein each of the subcutaneous injection of the second composition is carried out 1 week after the immediately preceding injection.

3. The method for treating Hunter syndrome according to claim 1,
   wherein the first composition is intravenously injected as a first once a week administration, and
   wherein the second composition is subcutaneously injected as subsequent once a week administrations, during a total of two-months administration of the first and the second compositions.

4. The method for treating Hunter syndrome according to claim 1, wherein the first composition is injected at an effective dose of 0.05 mg/kg to 20 mg/kg per week.

5. The method for treating Hunter syndrome according to claim 1, wherein the first composition is injected at an effective dose of 0.1 mg/kg to 5 mg/kg per week.

6. The method for treating Hunter syndrome according to claim 1, wherein the second composition is injected at an effective dose of 0.1 mg/kg to 40 mg/kg per week.

7. The method for treating Hunter syndrome according to claim 1, wherein the second composition is injected at an effective dose of 0.2 mg/kg to 10 mg/kg per week.

\* \* \* \* \*

SEQUENCE LISTING

<160> NUMBER OF SEQ ID NOS: 2

<210> SEQ ID NO 1
<211> LENGTH: 525
<212> TYPE: PRT
<213> ORGANISM: Homo sapiens

<400> SEQUENCE: 1

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
```

```
                180             185             190
Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
            290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
            370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
            450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro
            515                 520                 525

<210> SEQ ID NO 2
<211> LENGTH: 525
<212> TYPE: PRT
<213> ORGANISM: Artificial Sequence
<220> FEATURE:
<223> OTHER INFORMATION: Formylated IDS amino acid sequence
<220> FEATURE:
<221> NAME/KEY: MOD_RES
<222> LOCATION: (59)
<223> OTHER INFORMATION: FORMYLATION

<400> SEQUENCE: 2
```

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Gly Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
```

-continued

```
                420             425             430
Arg Glu Leu Ile Ala Tyr Ser Gln Tyr Pro Arg Pro Ser Asp Ile Pro
        435             440             445

Gln Trp Asn Ser Asp Lys Pro Ser Leu Lys Asp Ile Lys Ile Met Gly
        450             455             460

Tyr Ser Ile Arg Thr Ile Asp Tyr Arg Tyr Thr Val Trp Val Gly Phe
465             470             475             480

Asn Pro Asp Glu Phe Leu Ala Asn Phe Ser Asp Ile His Ala Gly Glu
                485             490             495

Leu Tyr Phe Val Asp Ser Asp Pro Leu Gln Asp His Asn Met Tyr Asn
            500             505             510

Asp Ser Gln Gly Gly Asp Leu Phe Gln Leu Leu Met Pro
        515             520             525
```